United States Patent [19]

Schramm

[11] Patent Number: 4,637,417

[45] Date of Patent: Jan. 20, 1987

[54] USE OF A SUBMERSIBLE VISCOMETER IN THE PRIMARY SEPARATION STEP OF THE HOT WATER PROCESS FOR RECOVERY OF BITUMEN FROM TAR SAND

[75] Inventor: Laurier L. Schramm, Edmonton, Canada

[73] Assignees: Alberta Energy Company Ltd.; Canadian Occidental Petroleum Ltd.; Esso Resources Canada Limited, all of Calgary; Gulf Canada Limited, Toronto; Her Majesty the Queen, in right of the Province of Alberta, as represented by the Minister of Energy and Natural Resources, Edmonton; HBOG-Oil Sands Limited Partnership, Calgary; PanCanadian Petroleum Limited, Calgary; Petro-Canada Inc., Calgary, all of Canada; a part interest

[21] Appl. No.: 730,173

[22] Filed: May 3, 1985

[51] Int. Cl.$^4$ .............................................. F17D 3/10
[52] U.S. Cl. ........................................ 137/4; 208/390; 208/401
[58] Field of Search .................... 137/4, 92; 73/54; 208/11 R

[56] References Cited

U.S. PATENT DOCUMENTS

| 3,380,463 | 4/1968 | Trethewey | 137/4 |
| 4,151,744 | 5/1979 | Hemmings | 73/54 |
| 4,200,550 | 4/1980 | Scherrer | 137/4 |
| 4,226,798 | 10/1980 | Cowfer et al. | 137/4 |

FOREIGN PATENT DOCUMENTS

| 841581 | 5/1970 | Canada . | |
| 889823 | 1/1972 | Canada . | |
| 889825 | 1/1972 | Canada . | |
| 2726228 | 12/1978 | Fed. Rep. of Germany | 73/54 |

Primary Examiner—Alan Cohan
Assistant Examiner—Sheri M. Novack
Attorney, Agent, or Firm—Millen & White

[57] ABSTRACT

The hot water process is controlled in response to viscosity measurements taken in situ in the middlings in the primary separation vessel. The viscosity in the middlings is found to vary. Therefore, the layer of maximum viscosity is located and the viscosity at this depth is monitored. Adjustments are made to the process to keep this maximum viscosity below a pre-determined limit.

2 Claims, 7 Drawing Figures

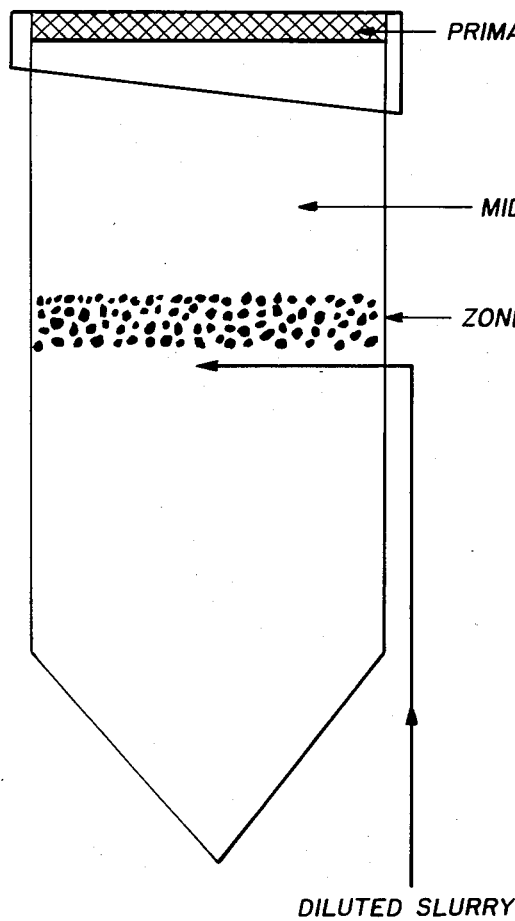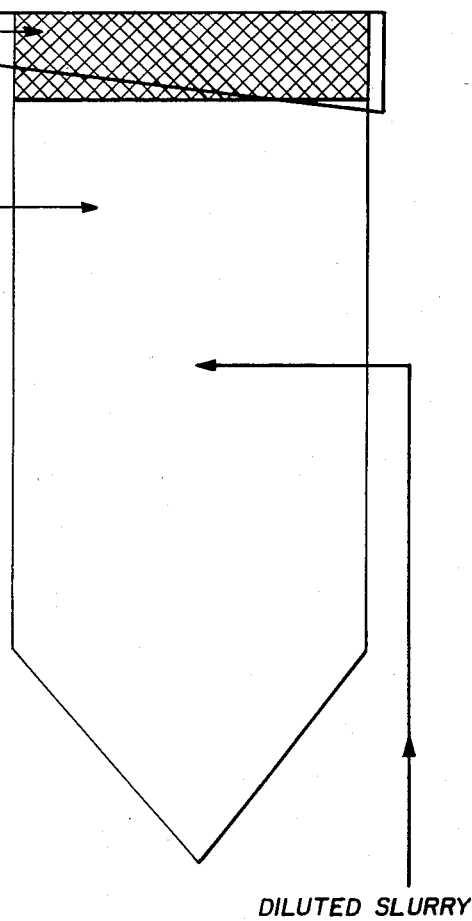

USE OF A SUBMERSIBLE VISCOMETER IN THE PRIMARY SEPARATION STEP OF THE HOT WATER PROCESS FOR RECOVERY OF BITUMEN FROM TAR SAND

FIELD OF THE INVENTION

This invention relates to an improvement of the flotation-sedimentation step, for recovering bitumen from a tar sand slurry in a primary separation vessel, which step forms part of a conventional tar sand plant circuit. More particularly, it relates to the manner in which the viscosity of the middlings is measured and to the utilization of the measurements so obtained to guide adjustments to the process conditions.

BACKGROUND OF THE INVENTION

Tar sands, also referred to as oil sands and bituminous sands, contain a heavy oil usually referred to as bitumen.

There are tar sand deposits, in the Athabasca region of Alberta, which are today being commercially exploited. In connection with these operations, the tar sand is first mined and the bitumen is then extracted from the mined tar sand by a process called the hot water process. The extracted bitumen is subsequently upgraded by refinerytype processing, to produce synthetic crude.

The tar sand is a mixture of sand grains, connate water, fine minerals of the particle size of clay, and bitumen. It is commonly believed that the connate water envelopes the grains of sand, the fine solids are distributed in the water sheaths, and the bitumen is trapped in the interstitial spaces between the water-sheathed grains.

The hot water process is now well described in the patent and technical literature. A schematic of the circuit is shown in FIG. 3.

In broad summary, this process comprises first conditioning the tar sand, to make it amenable to flotation-sedimentation separation of the bitumen from the solids. Conditioning involves feeding mined tar sand, hot water (180° F.), an alkaline process aid (usually NaOH), and steam into a rotating horizontal drum, wherein the ingredients are agitated together. Typically, the amounts of reagents added are in the following proportions:
 tar sand—3250 tons
 hot water—610 tons
 NaOH—4 tons (20% NaOH)
Enough steam is added to ensure an exit temperature of the mixture from the drum of about 180° F. The residence time in the drum is typically about 4 minutes.

During conditioning, the mined tar sand (in which the bitumen, connate water and solids are tightly bound together) is converted into an aqueous slurry of porridge-like consistency, wherein the components are in loose association.

The slurry leaving the drum is screened, to remove oversize material, and then flooded or diluted with additional hot water. The diluted slurry typically comprises 7% by weight bitumen, 43% water, and 50% solids. Its temperature is typically 160°–180° F.

The diluted slurry then is transferred to the primary separation step, wherein it is temporarily retained in a large separation vessel having a cylindrical upper section and conical lower section. (This vessel is hereafter referred to as the "PSV"—for 'primary separation vessel'.) The vessel is similar to a thickener and has a rake system in its lower end, to assist in discharging the sand bed which accumulates there. The slurry is retained in the PSV for about 45 minutes in a quiescent condition.

During this interval, air bubbles, incorporated into the dilute slurry during conditioning, attach themselves to the bitumen, which is in the form of flecks or globules. Most of the aerated globules are buoyant and they rise through the slurry, to collect at the upper surface in the form of a froth. This froth is referred to as primary froth.

Most of the coarse solids, primarily being sand particles, sink through the slurry, are concentrated in the conical bottom end of the vessel, and are discharged through a bottom outlet. This stream is discarded as tailings (known as the 'primary tailings').

Not all of the bitumen becomes sufficiently aerated so as to rise and join the primary froth. Some of this non-buoyant bitumen is lost with the primary tailings. Most of it, together with a large part of the fines, collects in the mid-section of the PSV. This aqueous mixture is termed "middlings".

A dragstream of the middlings is withdrawn from the vessel and is fed into subaerated flotation cells, wherein secondary separation is practised. Here the middlings are subjected to vigorous agitation and aeration. Bitumen froth, termed "secondary froth", is produced.

Typically, the primary and secondary froths have the following compositions:

|  | Primary (% by weight) | Secondary (% by weight) |
| --- | --- | --- |
| Bitumen | 66.4 | 23.8 |
| Solids | 8.9 | 17.5 |
| Water | 24.7 | 58.7 |

It will be noted that the secondary froth is considerably more contaminated with water and solids than the primary froth. One seeks to minimize this contamination, as the froth stream requires downstream treatment, to remove solids and water, before it can be fed to the upgrading process.

It is therefore desirable to operate the process so that as much of the bitumen as possible reports to the primary froth.

In summary then, the contents of the PSV may be described as existing in the form of three sequential layers. At the base, one has the tailings—this is primarily sand with some water and a minor amount of bitumen entrained therein. Above this layer, one has the middlings—this is water containing fines and insufficiently buoyant bitumen. But passing downwardly through the middlings are many coarse sand particles and rising through the layer are some buoyant bitumen globules. And at the top, one has the froth.

Of particular interest are the well-aerated bitumen globules, which should rise and form the primary froth, which is the main commercial product of the process. These globules must make their way up through the middlings.

If the middlings are too viscous, the well-aerated bitumen globules may fail to achieve the needed upward velocity, and may end up being discharged with the primary tailings or being withdrawn with middlings for treatment in the secondary separation circuit. If the globules exit with the primary tailings, they are lost entirely from the process. If they are removed to secondary recovery, they will be recovered in the form of poor quality froth.

At this point, it is appropriate to point out: (1) that the nature of the tar sand feed is variable; and (2) that the capability of the hot water process to extract the contained bitumen is significantly affected by the nature of the tar sand feed.

More particularly, the tar sand may contain a relatively high content of bitumen and a relatively-low content of fines. This type of feed is referred to as "rich" tar sand. Alternatively, the tar sand may be relatively low in bitumen and high in fines. Such a feed is referred to as "lean" tar sand.

Typically, a "rich" tar sand can have a composition as follows:
14.44%—bitumen
0.36%—water
85.2%—total solids Typically, a "lean" tar sand can have a composition as follows:
7.56%—bitumen
0.5%—water
91.84%—total solids.

The percentage fine solids ($-44\mu$ solids in the total solids) can range from 5% for rich tar sands to as high as 25% for some lean tar sands.

In general, the rich tar sand feeds yield high primary froth recoveries. The lean feeds give low primary froth recoveries. Stated otherwise, the lean feeds are difficult to process with the hot water extraction procedure; they do not contain much bitumen and such bitumen as they do contain is difficult to extract.

This is partly because the lean feeds contain many fines, which interfere with the flotation-sedimentation separation taking place in the middlings layer of the PSV. In addition, the flecks or globules of bitumen which appear in the PSV middlings, when lean tar sand is the feed, are minute compared to the globules that are there when the tar sand feed is rich. These minute flecks do not rise as readily as the larger flecks.

If the fines content in the middlings becomes high, the flotation mechanism can literally become inoperative. There is so little primary froth being produced that the process performance is unacceptable. In this instance, the contents of the PSV may have to be jettisoned and the process started up again.

There are a number of courses of action open to the operator by which he may adjust and alleviate undesirable process conditions in the PSV arising from the nature of the tar sand feed. For example, he can:
 adjust the rate of NaOH addition; or
 adjust the rate of water addition to the conditioning or flooding steps; or
 blend some better quality tar sand in with the lean tar sand, to provide a blended feed; or
 vary the residence time or temperature in the conditioning drum.

A crucial matter, though, is to know when to make these adjustments and to what extent the adjustment should be made. This requires that a process parameter be monitored, which parameter gives the operator a useful guide on which to base the adjustments.

It has heretofore been broadly taught in the prior art that the viscosity of the middlings can be monitored and maintained within staged ranges, to optimize the primary bitumen froth recovery from the PSV. This teaching appears in Canadian Pat. No. 889,823, filed by Graybill et al. Also of interest are Canadian Pat. Nos. 889,825 and 841,581.

However, in accordance with conventional practise, the viscosity has been monitored in one of the following ways:
 withdrawing a sample from the middlings dragstream and measuring the sample viscosity with an appropriate instrument; or
 lowering a sampler into the middlings, taking a grab sample, and measuring the sample viscosity with an appropriate instrument; or
 applying density measurements to either of the foregoing samples and assuming that the viscosity varies proportionately with the density.

Now, there are certain shortcomings associated with these prior art practises.

If one samples the middlings dragstream, one must assume that this sample—taken at one level of the PSV (there is usually only a single outlet in the PSV wall)—is representative of the entire column of PSV middlings.

When one attempts to measure the viscosity of this sample, one is dealing with a mixture of sand, oil, clay, and water. The sand and oil begin to settle and rise instantaneously. In addition, the mixture is not static. It is impossible to duplicate the flow and turbulence conditions which exist within the PSV.

Perhaps for these reasons, the industry has moved toward measuring the density of the sample and assuming that the trend of viscosity will follow the trend of density.

SUMMARY OF THE INVENTION

In the fundamental step of this invention, the viscosity of the middlings is taken in situ in the PSV with a submersible viscometer.

In the testing which led up to this invention, when this was done the following discoveries were made:
 (1) that the viscosity varies strikingly at various depths in the middlings in the PSV;
 (2) that while the in situ-measured viscosity in the PSV may vary significantly, the density of the middlings when measured in connection with grab samples may vary very little—therefore there does not appear to be a useful correlation between the two that may be relied on; and
 (3) that the viscosity measurements obtained in situ vary significantly from those obtained by taking grab samples at the same depth in the PSV and measuring the viscosity of the grab samples in a conventional instrument external of the PSV.

Stated otherwise, it has been found that it is necessary to measure the viscosity of the middlings in the dynamic environment of the PSV contents, in order to obtain reliable and useful measurements. It is postulated that the currents which arise in the PSV (from the continuous entry of fresh slurry, the withdrawals of the tailings and middlings streams, and the influences of dropping solids and rising bitumen), together with the presence of the solids at the point of testing, combine to create a unique and depth-variable viscosity regime in situ which differs in kind from that which may be measured in grab samples and dragstreams. It is this unique in situ viscosity regime which must be monitored in order to give the desired guidance for process control.

In a preferred embodiment, one may "hunt" out the maximum viscosity level in the middlings in the PSV by moving the submersible viscometer vertically and taking measurements at different levels. One then alleviates the undesirable process conditions by monitoring viscosity at this level and making one or more process adjustments, as previously described, to control said maximum viscosity and bring it close to a pre-determined desired value.

Broadly stated, the invention is an improvement in the primary separation step of the hot water process for extracting bitumen from tar sand in a primary separation vessel, wherein the bitumen floats upwardly in a tar sand slurry to form a froth layer, the coarse solids drop to form a tailings layer, and a middlings layer is formed between the froth and the tailings. The improvement comprises: providing a submerged viscometer in the middlings layer and actuating said viscometer to measure the viscosity of the middlings at one or more levels in the vertical column of middlings and produce signals, external of the vessel, which are indicative of said measurements; and adjusting the viscosity of the middlings in response to said signals to maintain the maximum viscosity in the column below a pre-determined value.

DESCRIPTION OF THE DRAWINGS

FIG. 6a is a fanciful representation of the PSV contents during the run in which NaOH was not used;

FIG. 6b is a fanciful representation of the PSV contents during the run in which NaOH was used.

DESCRIPTION OF THE PREFERRED EMBODIMENT

Figure 1:
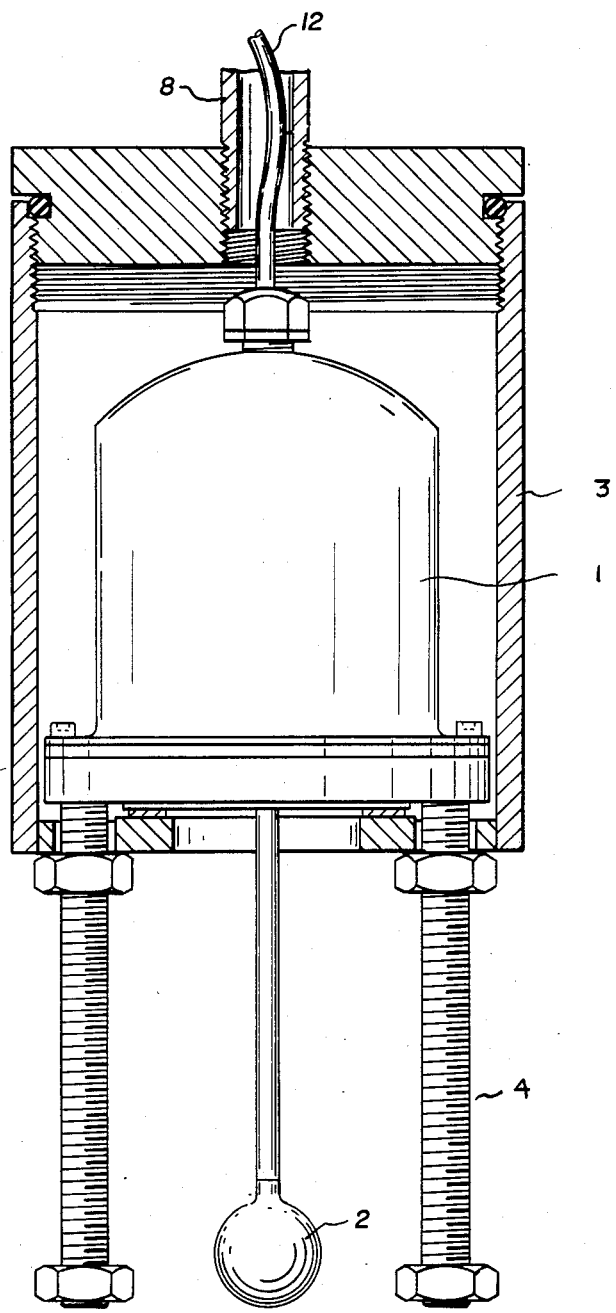
FIG. 1 is a partially sectional side view of the viscometer used in connection with the invention.

The viscometer 1 used was of the oscillating torsional pendulum type. The particular viscometer used was obtained from Nametre Co., Edison, N.J. and was identified as Model 7-006. This particular viscometer has a sphere 2 which vibrates at a certain frequency in air. When the viscometer is immersed in a viscous medium, there is a change or diminuation in vibration amplitude, which is related to the drag on the sphere. The additional power required, to maintain the amplitude, with the sphere immersed, at its value in air, is a measure of the viscosity of the medium.

The mode of operation of this instrument is explained in an article entitled "New technique accurately measures low viscosity on-line" in Control Engineering, July, 1975, pp. 39-40, which article is incorporated herein by reference.

The viscometer 1 was enclosed in a waterproof housing 3. Protective threaded bars 4, adjustable in length, were screwed into the housing 3 and protruded downwardly beside the sphere 2, to protect it against contact with the wall 5 and rake 6 of the PSV 7. A tube 8 was attached to the housing 3, whereby the unit could be raised and lowered—conductive leads 12 extended through the tube 8 to the viscometer. The viscometer was adapted to produce a signal, indicative of the change in vibration amplitude exerted by the PSV fluid, which signal was a measure of the viscosity of the fluid in which the sphere 2 was vibrating.

Figure 2:
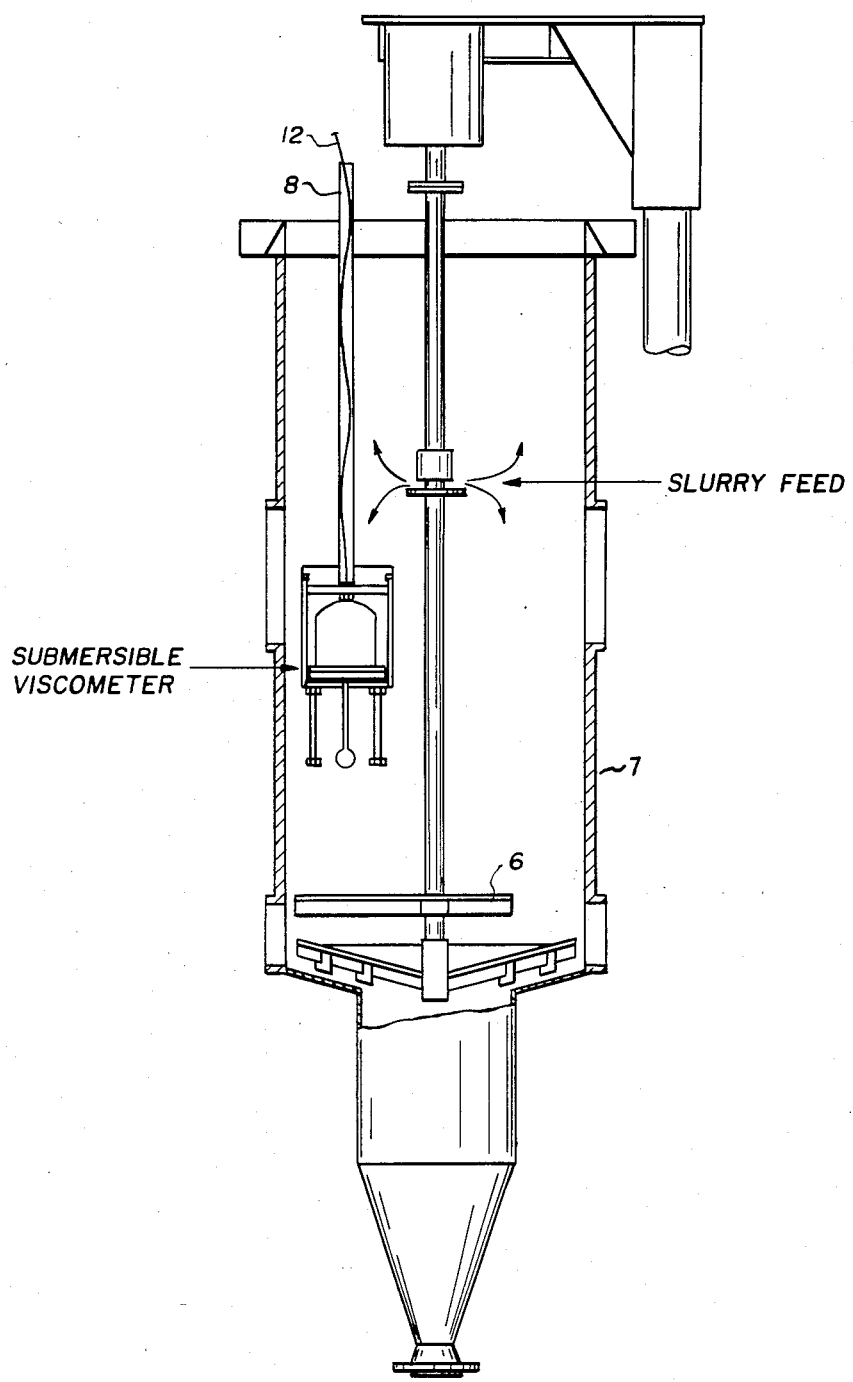
FIG. 2 is a sectional side view showing the viscometer suspended in the PSV of the pilot hot water process circuit used in developing the invention.

The viscometer 1 is shown in FIG. 2 as it was used in the PSV 7. This PSV was a small, non-commercial pilot unit. However, processing results in this pilot unit had previously been shown to correlate with processing results in applicant's full scale commercial PSVs.

The pilot PSV 7 was glass-sided, so that the action within could be observed.

Figure 3:
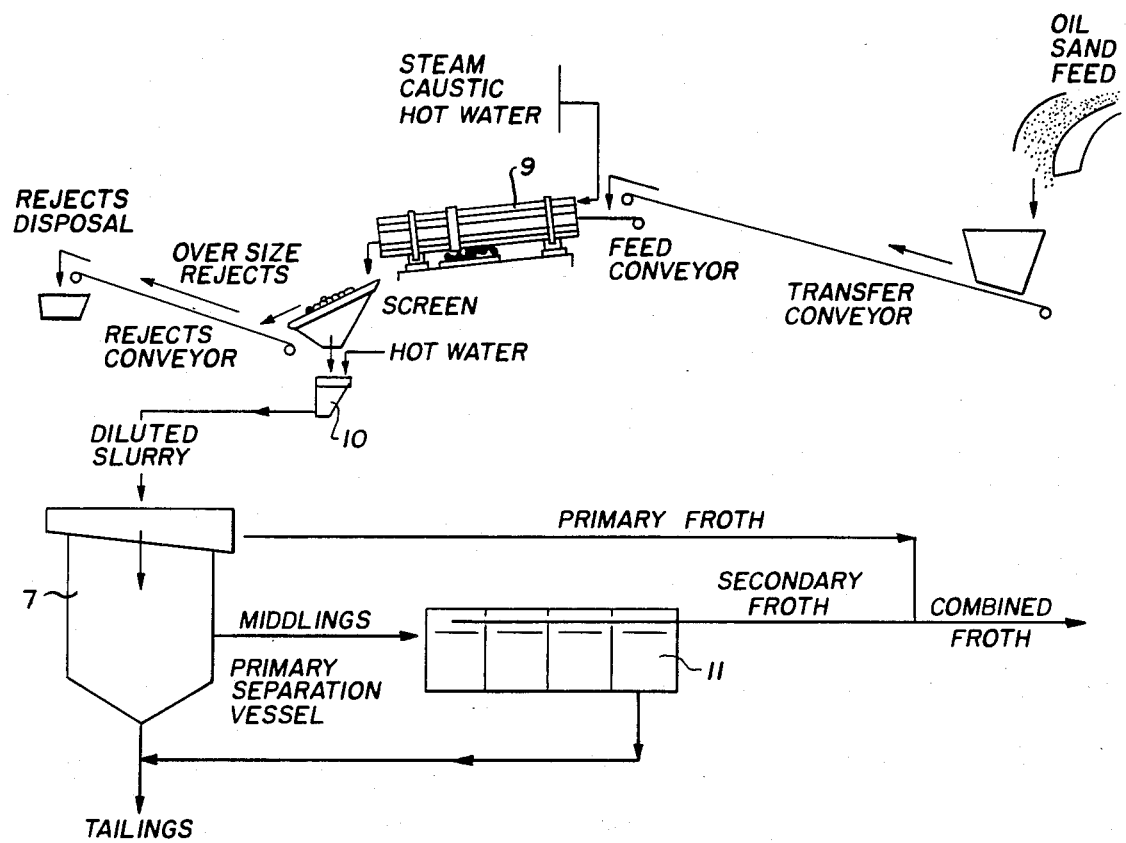
FIG. 3 is a schematic showing the hot water process circuit.

The PSV 7 was part of a circuit illustrated in FIG. 3. This circuit comprised a tumbler 9, in which tar sand was mixed with hot water, NaOH, and steam, and conditioned. The product slurry from the tumbler 9 was diluted with additional hot water in a pump box 10. The diluted slurry from the pump box 10 was transferred into the PSV 7 and retained there under quiescent conditions, to produce bitumen, froth, tailings, and middlings. Middlings were withdrawn from the PSV 7 and treated in a bank of sub-aerated flotation cells 11, to produce secondary froth and secondary tailings. The foregoing steps were conducted in accordance with conventional hot water process conditions.

EXAMPLE 1

Figure 4:
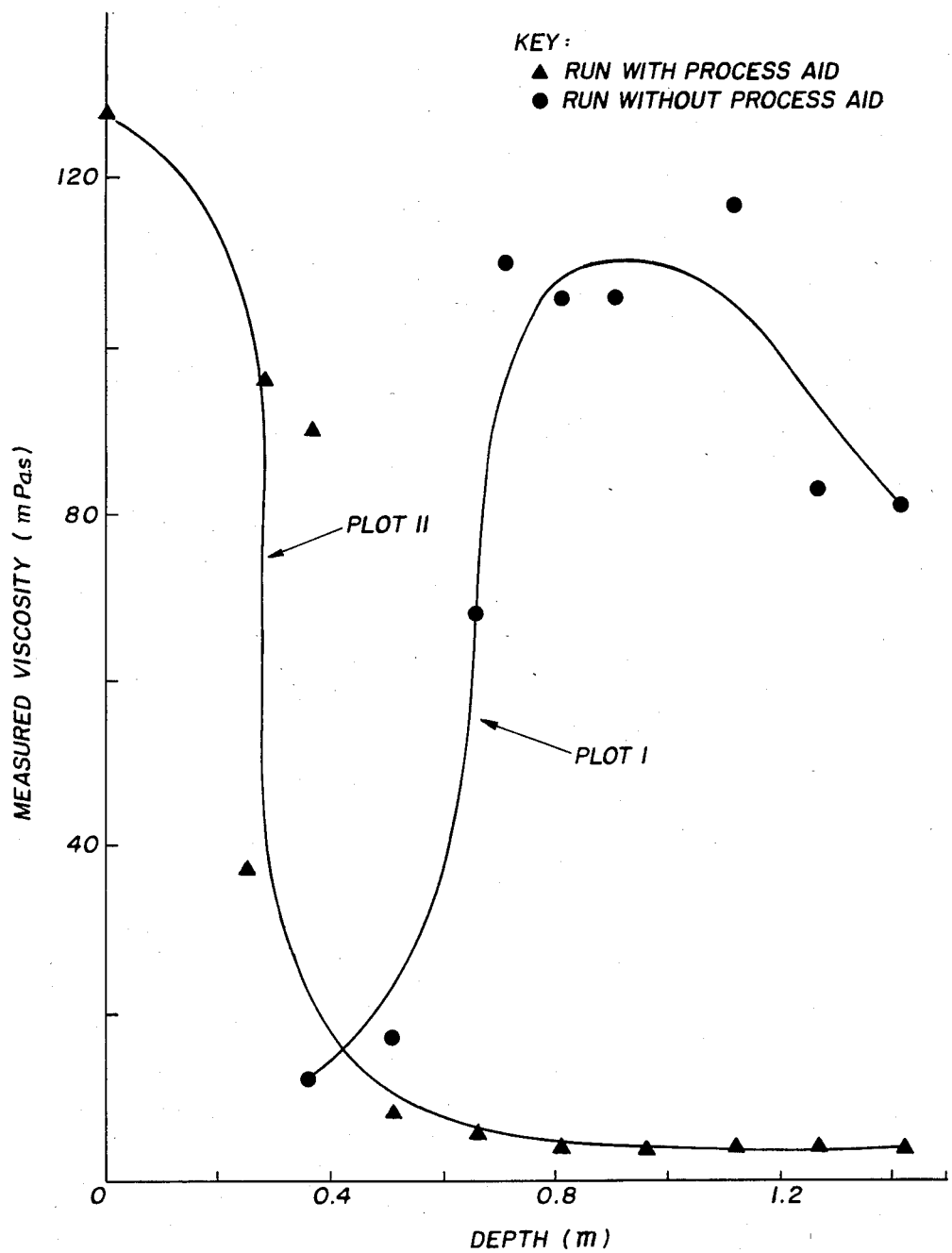
FIG. 4 is a plot of measured in-situ viscosity versus depth in the PSV at which the viscosity was measured, showing the variation in viscosity which is present in the PSV middlings at different levels, for a single tar sand feed treated in two ways—one without NaOH addition and the other with NaOH.
Figure 5:
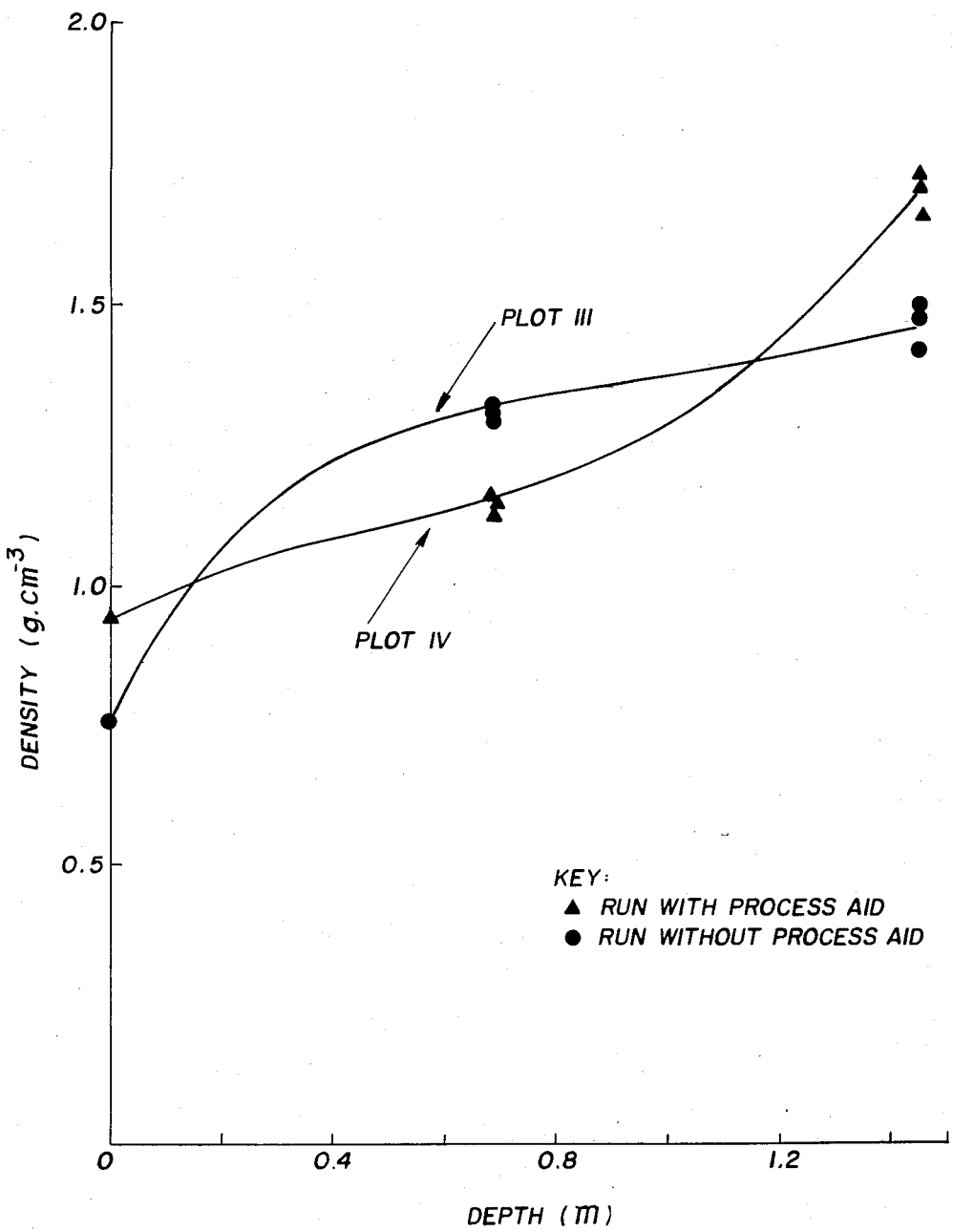
FIG. 5 is a plot of measured density values for grab samples taken at different depths for the tar sand runs which generated the data for FIG. 4.

The pilot circuit was used to process a tar sand designated "A". This was known to be a poorly processing, lean feed. Two runs were made during which the feed was treated by the hot water process. One run was carried out with NaOH process aid having been incorporated in the slurry; the other run was carried out without NaOH. Viscosity measurements were made during each run using the viscometer 1 at different depths in the middlings in the PSV 7. Two curves or plots of measured in situ viscosity versus depth were developed. Plot 1 in FIG. 4 involved the run without NaOH. Plot 2 in FIG. 4 involved the run with NaOH. The details of the conditions and primary froth recovery results of the two runs are now set forth.

Tar Sand "A" composition:
9.8% bitumen
3.2% water
87.0% solids
21.3% fine solids (expressed as % of $-44\mu$ solids in the total solids)

| Pilot Processing of Oil Sands "A" | |
|---|---|
| Oil Sand Feed Rate - 630 g/s | |
| Slurry Temperature - 80° C. | |
| Rate of Total Water Addition - 418 g/s | |
| NaOH Addition (wt. %) | Primary Bitumen Recovery (%) |
| 0.000 | 9.5 |
| 0.025 | 22.1 |

As shown by plot 1 for the run without NaOH, at a depth of about 0.4 m in the PSV, the viscosity measured with the viscometer was about 15 mPa.s. As the viscometer was lowered, the viscosity increased rapidly to 110 mPa.s. at a depth of 0.8 m, and then diminished to about 80 mPa.s. at a final depth of about 1.2 m.

Thus the PSV contents, when the PSV was operating on this lean tar sand A, were shown to be characterized by:

a low viscosity at the upper end of the body of contents (as very little primary bitumen froth was generated by the poorly processing slurry in the absence of NaOH);

changes in viscosity with depth;

and a "plug" or layer of nigh viscosity middlings intermediate its ends.

The PSV contents were visually observed through the glass wall of the vessel. FIG. 6a depicts what was observed. Again, there was only a thin layer of primary bitumen froth at the top end of the vessel contents and a viscous intermediate layer, which contained much bitumen.

The same tar sand A was then treated under the same conditions as the Plot 1 run, except that in this second run a conventional amount of NaOH was used. The in-situ viscosity versus depth results are shown by Plot II in FIG. 4. At the top of the cell contents the viscometer 1 indicated a high viscosity (130 mPa.s.), indicative of the thick bitumen froth layer which was produced. As the viscometer was lowered to 0.3 m, it passed through the froth-middlings interface and the measured viscosity dropped off sharply. The viscometer 1 indicated that the viscosity continued to decline to a limiting value around 10 mPa.s. in the lower part of the vessel. There was no "plug" of highly viscous middlings to hinder the rise of the bitumen globules. An improved primary bitumen froth recovery was obtained in this run as compared with the first run. Visual inspection during the run indicated that the PSV contents were of the form shown in FIG. 6b. There was a thick froth layer and no noticeable viscous layer laden with bitumen.

Thus there was correlation between the results indicated by the in situ viscometer measurements and PSV performance as indicated by the primary oil recoveries.

During the two runs, several grab samples were also taken at depths corresponding with some of those at which the viscometer 1 took in situ measurements. Attempts to measure viscosity representative of conditions within the PSV, on withdrawn samples, resulted in failure. The above-noted problems, that is, the ascent of bitumen in the sample jars, the rapid settling of coarse solids, and the impractical requirements for reproducing the flow and turbulence currents of the PSV, caused such measurements to be abandoned.

In summary, these results show that:

(1) use of the submersible viscometer produces results that indicate that there are viscosity changes that occur within a PSV with depth;

(2) If high viscosity layers are developed in the PSV middlings, they do trap bitumen and diminish primary bitumen froth production; and (3) These high viscosity layers can be eliminated by adjusting process conditions, thereby improving primary bitumen froth recovery.

In use, the signals emitted by the viscometer 1, submerged in the middlings, are monitored and the viscosity of the middlings are adjusted by altering one of the aforesaid process conditions, to maintain the maximum viscosity in the middlings column below a predetermined value.

The embodiments of the invention in which an exclusive property or privilege is claimed are defined as follows:

1. In the primary separation step of the hot water process for extracting bitumen from tar sand in primary separation vessel, wherein the bitumen floats upwardly in a tar sand slurry to form a froth layer, the coarse solids drop to form a tailings layer, and a middlings layer is formed between the froth and the tailings, the improvement comprising:

providing a submerged viscometer in the middlings layer and actuating said viscometer to measure the viscosity of the middlings at one or more levels in the vertical column of middlings and produce signals, external of the vessel, which are indicative of said measurements;

taking sufficient measurements to determine the viscosity of the region of maximum viscosity within the middlings layer and adjusting the viscosity of the middlings in response to said signals to maintain the maximum viscosity in the column below a predetermined value, whereby the flotation of the bitumen through the middlings layer to the froth layer is substantially enhanced.

2. The improvement as set forth in claim 1 comprising:

moving the viscometer vertically within the column of middlings and locating and measuring the viscosity of the layer of middlings which has the maximum viscosity.

* * * * *